(12) United States Patent
Shang

(10) Patent No.: US 12,155,173 B2
(45) Date of Patent: Nov. 26, 2024

(54) COMBINED MULTI-WAVELENGTH LASER

(71) Applicant: Hua Shang, Nanjing (CN)

(72) Inventor: Hua Shang, Nanjing (CN)

(73) Assignee: Hua Shang (CN)

( * ) Notice: Subject to any disclaimer, the term of this patent is extended or adjusted under 35 U.S.C. 154(b) by 0 days.

(21) Appl. No.: 17/613,845

(22) PCT Filed: Sep. 7, 2021

(86) PCT No.: PCT/CN2021/116906
§ 371 (c)(1),
(2) Date: Nov. 23, 2021

(87) PCT Pub. No.: WO2023/029062
PCT Pub. Date: Mar. 9, 2023

(65) Prior Publication Data
US 2024/0030680 A1    Jan. 25, 2024

(30) Foreign Application Priority Data

Sep. 1, 2021   (CN) .......................... 202111019916.8

(51) Int. Cl.
*H01S 5/042* (2006.01)
*A61N 5/06* (2006.01)
*A61N 5/067* (2006.01)
*H01S 5/40* (2006.01)

(52) U.S. Cl.
CPC .............. *H01S 5/042* (2013.01); *A61N 5/067* (2021.08); *H01S 5/4087* (2013.01); *A61N 5/062* (2013.01); *A61N 2005/0663* (2013.01)

(58) Field of Classification Search
CPC .............................. H01S 5/4087; H01S 5/042
See application file for complete search history.

(56) References Cited

U.S. PATENT DOCUMENTS

| 10,918,881 | B1 * | 2/2021 | Shang | A61N 5/062 |
| 2020/0054891 | A1 * | 2/2020 | Park | A61N 5/0603 |
| 2021/0268305 | A1 * | 9/2021 | Karavitis | A61B 18/20 |

* cited by examiner

Primary Examiner — Michael Carter
(74) Attorney, Agent, or Firm — Dickinson Wright PLLC

(57) ABSTRACT

A combined multi-wavelength laser with a laser module, a power supply module, and a communication module is disclosed. The power supply module is used to power the laser module and the communication module and includes a power supply controller, a power supply bus, and an independent power source connector. The power supply controller is connected to the independent power source connector via the power supply bus. The communication module includes a communication controller, a communication bus, and an independent communication connector. The communication controller is connected to the independent communication connector through the communication bus. The communication module and the power supply module are provided with branch lines so that multiple lasers can communicate in parallel and the independent communication and independent power supply of any one laser can control multiple lasers to realize a photodynamic therapy laser with functions of multi-wavelength emission, laser detachable and wavelength switching.

9 Claims, 9 Drawing Sheets

COMBINED MULTI-WAVELENGTH LASER

CROSS-REFERENCE TO RELATED APPLICATION(S)

This application is the U.S. National Phase of PCT/CN2021/116906, filed Sep. 7, 2021, which claims priority to Chinese Application No. CN202111019916.8, filed Sep. 1, 2021, the disclosures of which are incorporated herein by reference in their entireties.

FIELD

The embodiment of the present invention relates to the technical field of lasers, in particular to a combined multi-wavelength laser.

BACKGROUND

Photodynamic Therapy (PDT) is a new technology that uses photodynamic effects for disease diagnosis and treatment based on the photodynamic effect, which is a photosensitization reaction accompanied by biological effects involving aerobic molecules. The process of which is that a specific wavelength of laser irradiation causes the photosensitizer absorbed by the tissue to be excited, and the excited photosensitizer transfers energy to the surrounding oxygen to generate highly active singlet oxygen. Oxidation reaction is performed between singlet oxygen and neighboring organisms to produce cytotoxicity, which in turn leads to cell damage and even death. Compared with traditional therapies, photodynamic therapy has the advantages of less trauma, good targeting, no drug resistance and toxic side effects.

Visible red light is often used as the illumination light. Most photosensitizers can strongly absorb light at or longer than 630 nm. Laser is the most convenient and portable light source. It is coherent and monochromatic, that is, it produces high-energy single-wavelength light waves, and the output power of which can be precisely adjusted. It can directly pass through fiber optic cables to be introduced into hollow organs and deep within the tumor. Diode lasers are cheaper than metal vapor lasers or tuned-dye lasers and are portable, so they are often used. The treatment time of photodynamics is related to the ability of the photosensitizer to absorb light and the effectiveness of light to transfer energy to oxygen.

Depending on the indication in treatment and the type of photosensitizer, the laser wavelength and required energy are also different. For example, Photofrin is a photosensitizer for gastric cancer and bladder cancer with an excitation wavelength of 630 nm; Metvix is a photosensitizer for basal cell carcinoma with an excitation wavelength of 635 nm; Foscan is a photosensitizer for head and neck tumors with an excitation wavelength of 652 nm; Purlytin is a photosensitizer for breast cancer and prostate cancer with an excitation wavelength of 664 nm; Talaporfin is a broad-spectrum photosensitizer for solid tumors with an excitation wavelength of 664 nm; Verteporfin is a photosensitizer for basal cell carcinoma with an excitation wavelength of 689 nm; Lutex is a photosensitizer for prostate cancer and brain cancer with an excitation wavelength of 732 nm.

According to the advantages and disadvantages of lasers in medical treatment summarized by the American Cancer Society, the biggest problem with lasers for medical treatment is that the lasers are complex in structure, expensive, and cumbersome steps in use. Medical staff generally lack of training and fear in the use of medical laser, which seriously hinders the popularization of laser therapeutic apparatus in medical treatment. Especially for photodynamic therapy, there are many types of photosensitizers and applicable diseases, and new photosensitizers are constantly being launched on the market. Ordinary medical staff who do not have common knowledge of lasers are often helpless or prone to make mistakes when changing lasers or changing laser wavelengths.

At present, there is no photodynamic therapy laser capable of multi-wavelength emission, wavelength switching and detachable on the market. For example, DIOMED's DIOMED 630 PDT Laser is a photodynamic laser dedicated to Photofrin with an emission wavelength of 630 nm; the XD-635AB photodynamic laser therapeutic apparatus produced by Guilin Xingda Pharmaceutical Co., Ltd., China has an emission wavelength of 630 nm and an optical output with an optical fiber core diameter of 400 um. Lasers used in photodynamic therapeutic apparatus are generally semiconductor lasers, which is output through optical fiber coupling. The coupling output interface between semiconductor laser and optical fiber and the coupling output port between optical fiber and optical fiber need precise mechanical cooperation to achieve high coupling efficiency. Therefore, the fixed structure tightened by mechanical thread is generally adopted. Unless professionals use professional tools, semiconductor lasers are difficult to replace in the therapeutic apparatus. When semiconductor lasers of different wavelengths are used to form one therapeutic apparatus, the optical fiber of which has multiple ports, which makes it difficult to perform flexible wavelength switching.

SUMMARY

To this end, an embodiment of the present invention provides a combined multi-wavelength laser, which realizes a photodynamic therapy laser with functions of multi-wavelength emission, laser detachable, and wavelength switching.

In order to achieve the foregoing objective, the embodiments of the present invention provide the following technical solutions:

A combined multi-wavelength laser provided with a laser module, a power supply module, and a communication module, the power supply module is used to power the laser module and the communication module, wherein the power supply module includes a power supply controller, a power supply bus, and an independent power source connector, the power supply controller is connected to the independent power source connector via the power supply bus, the power supply bus is provided with a conductive branch line, and the outer end of the conductive branch line is provided with a wire connector; the communication module includes a communication controller, a communication bus, and an independent communication connector, the communication controller is connected to the independent communication connector through the communication bus, the communication bus is provided with a communication branch line, the outer end of the communication branch line is provided with a communication connector.

Further, the power supply bus is provided with two sets of conductive branch lines, wherein one set of the conductive branch lines is connected to a first wire connector, and the other set of the conductive branch lines is connected to a second wire connector, and the first wire connector and the second wire connector are in a matching connection relationship with each other.

Further, the communication bus is provided with two sets of communication branch lines, one set of the communication branch lines is connected to a first communication connector, and the other set of the communication branch lines is connected to a second communication connector, and the first communication connector and the second communication connector are in a matching connection relationship with each other.

Further, the external of the combined multi-wavelength laser is provided with a mechanical connector, and the mechanical connector is used for a fixed connection between two combined wavelength lasers.

Further, a rotatable magnet and a rotating structure for controlling the rotation of the magnet are provided in the mechanical connector, and the magnet is provided with a magnetic surface and a non-magnetic surface, the connecting side of the mechanical connector is provided with a slot-shaped structure exposing the magnet.

Further, the rotating structure comprises a rotating shaft located on both sides of the magnet, and the rotating shaft is connected to the mechanical connector in rotation, and the rotating shaft is provided with a non-circular groove, a through hole exposing the non-circular groove is provided on the mechanical connector, and a crank is inserted into the non-circular groove.

Further, the rotating shaft is provided with a limiting protrusion, and the mechanical connector is provided with an arc-shaped slot that matches with the limiting protrusion, the arc of the arc-shaped slot is the same as the arc corresponding to the rotation angle of the magnet.

Further, the power connector or communication connector is provided on the mechanical connector.

Further, the rotating shaft is provided with a driving gear which meshes with a driven rack, and the driven rack is fixed on one side of an insulating base, the parallel power supply connector or parallel communication connector is installed on the insulating base.

The embodiments of the present invention have the following advantages:

The combined multi-wavelength laser according to the embodiment of the present invention is provided with a laser module, a power supply module, and a communication module, so that the communication module analyzes and processes the control signal of the upper computer and sends it to the power supply module, and the power supply module controls or adjusts the power supply of the laser module according to control signals. Both the communication module and the power supply module are provided with branch lines, so that multiple lasers can be connected in parallel. The independent communication and power supply of any one laser can control multiple lasers, thereby achieving a photodynamic therapy laser with functions of multi-wavelength emission, laser detachable and wavelength switching.

The shape and output interface of the combined multi-wavelength laser according to the embodiment of the present invention are kept uniform, and installation can be performed through mechanical connectors to realize convenient detachment and replacement. Then, the multi-wavelength laser output through the laser array is output to the wavelength switcher through multiple optical fibers. The wavelength switcher has one output optical fiber, one of the input optical fibers is coupled with the output optical fiber through the mechanical structure, and the output laser wavelength is switched by switching the coupling between the input optical fiber and the output optical fiber. The wavelength switcher can also have multiple output optical fibers, the switching of input wavelength and output wavelength is realized by the same principle, so as to realize a photodynamic therapy laser with multi-wavelength emission, detachable laser, and wavelength switching.

BRIEF DESCRIPTION OF DRAWINGS

In order to illustrate the examples of the present invention or the technical solutions in the prior art more clearly, the drawings that need to be used in the description of the examples or the prior art will be briefly introduced in the following. Obviously, the drawings described in the following are only exemplary, and other implementation drawings can be derived from the provided drawings for those of ordinary skill in the art without creative work.

The structure, proportion, size, etc. shown in this specification are only used to match the content disclosed in the specification for the understanding and reading of those who are familiar with this technology. They are not used to limit the limitations of the implementation of the present invention, so they are not of technical significance. Any modification of structure, change of proportional relationship or adjustment of size, without affecting the effects and objectives that can be achieved by the present invention, should still fall within the scope of the technical content disclosed in the present invention.

In the figures.

1: laser module; 2: optical fiber interface; 3: heat dissipating fan; 4: power supply controller; 5: power supply bus; 6: independent power supply connector; 7: power supply branch line; 8: parallel power supply connector; 9: power supply indicator; 10: light emitting indicator; 11: communication controller; 12: communication bus; 13: independent communication connector; 14: communication branch line; 15: parallel communication connector; 16: mechanical connector; 17: magnet; 18: magnetic surface; 19: non-magnetic surface; 20: slot-shaped structure; 21: rotating shaft; 22: non-circular groove; 23: crank; 24: arc-shaped protrusion; 25: rectangular-shaped protrusion; 26: arc-shaped slot 27: driving gear; 28: insulating base; 29: driven rack; 30: first parallel power supply connector; 31: second parallel power supply connector; 32: first parallel communication connector; 33: second parallel communication connector.

DETAILED DESCRIPTION

The following specific examples illustrate the implementation of the present invention. Those familiar with this technology can easily understand the other advantages and effects of the present invention from the contents disclosed in this specification. Obviously, the described examples are part, not all, of the examples of the present invention. Based on the examples of the present invention, all other examples obtained by those of ordinary skill in the art without creative work shall fall within the protection scope of the present invention.

Figure 1:
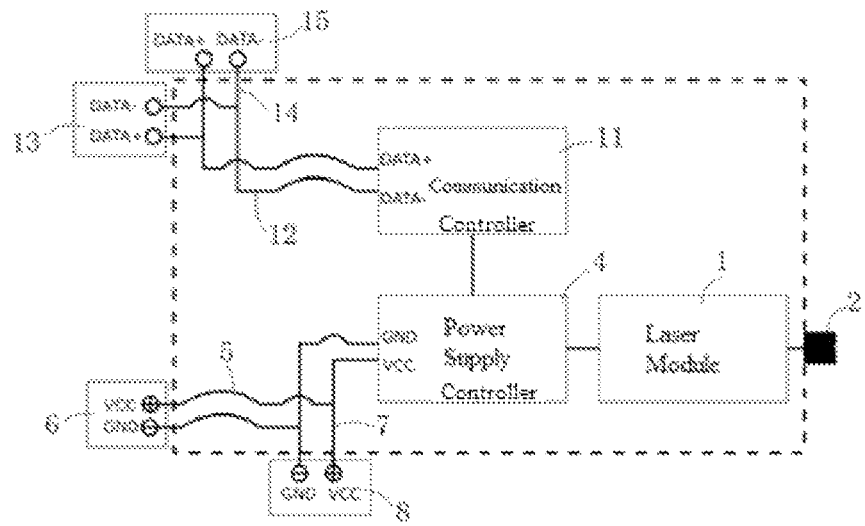
FIG. 1 is a system structure diagram of a combined multi-wavelength laser provided by an example of the present invention.
Figure 2:
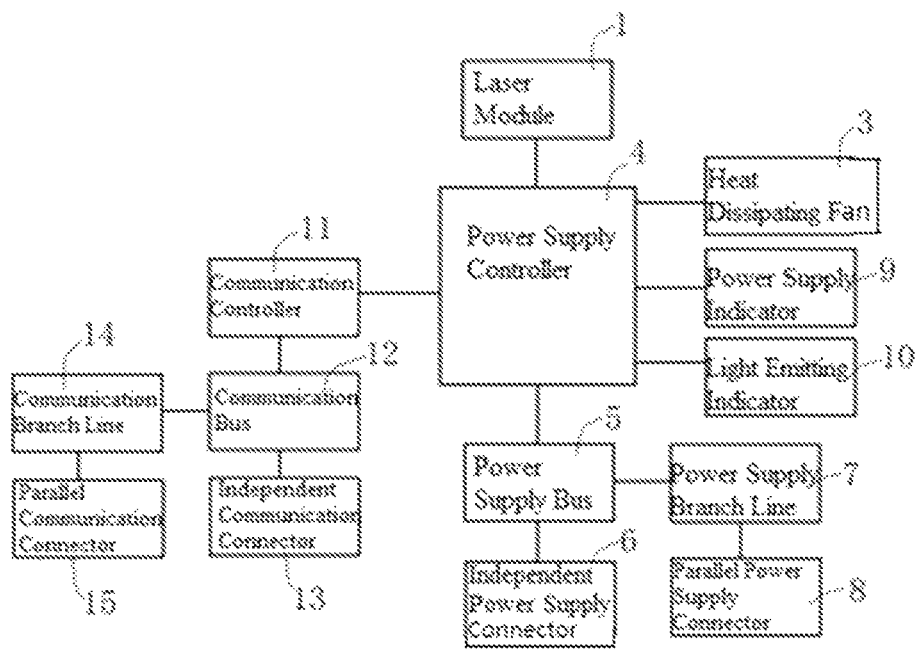
FIG. 2 is a system block diagram of FIG. 1.

As shown in FIGS. 1-2, a combined multi-wavelength laser is provided with a laser module 1, a power supply module, and a communication module. The power supply module is used to supply power to the laser module 1 and the communication module. The communication module is used to analyze and process the control signal of the upper computer and send it to the power supply module. The power supply module controls or adjusts the power supply of the laser module 1 according to the control signal. In this example, the power supply module is connected to the laser module 1 and the communication module, respectively.

Figure 5:
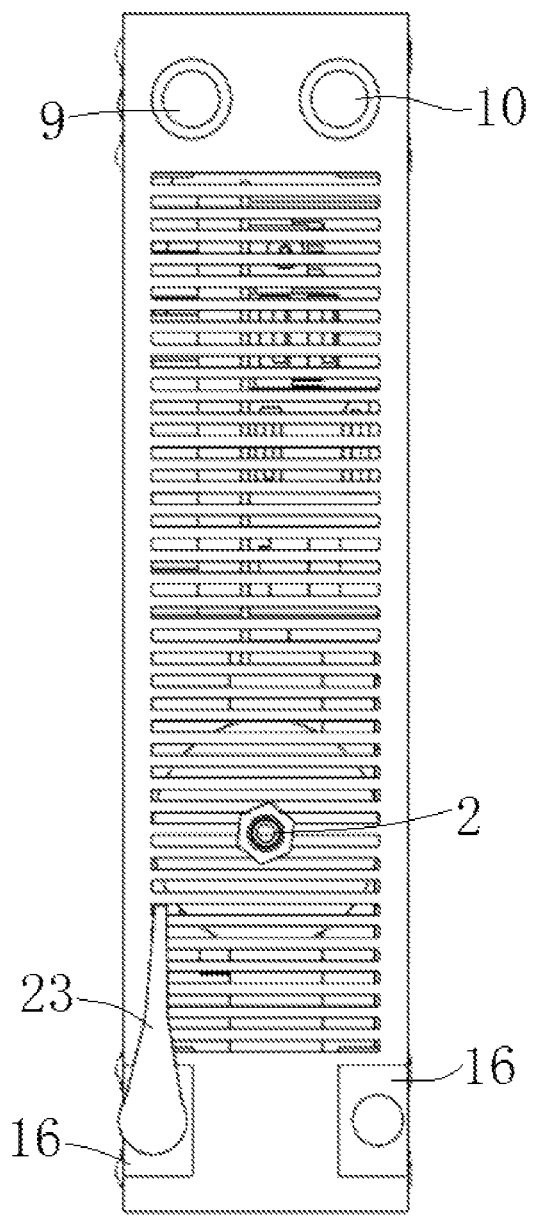
FIG. 5 is a front view of a product of a combined multi-wavelength laser provided by an example of the present invention.
Figure 6:
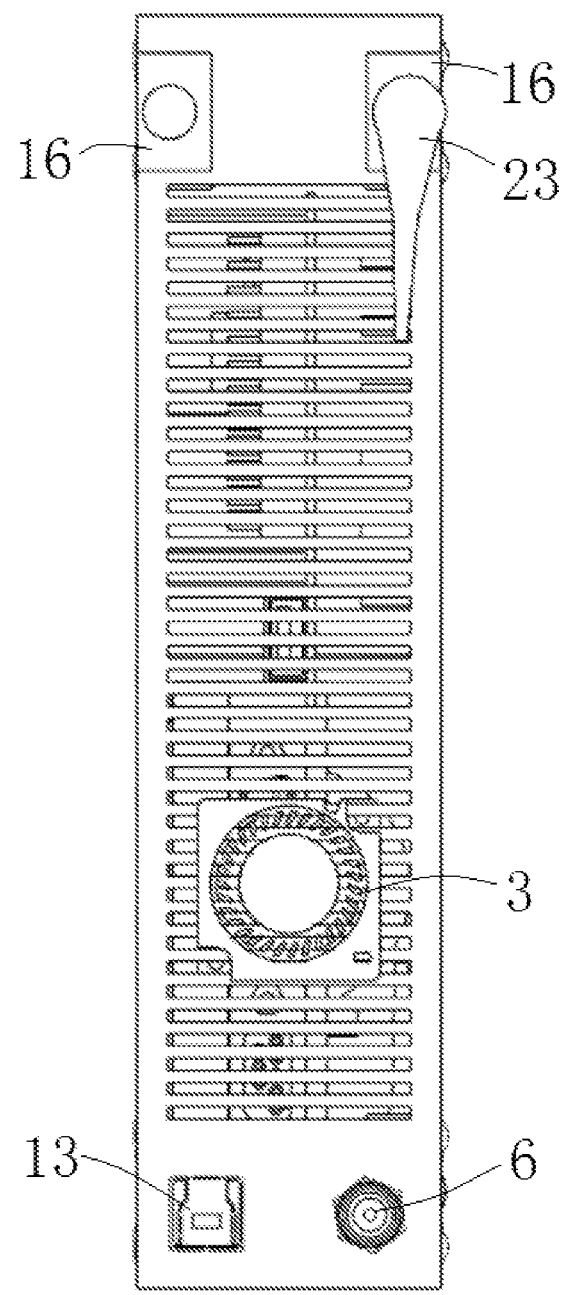
FIG. 6 is a rear view of a product of a combined multi-wavelength laser provided by an example of the present invention.

In this example, the laser module 1 adopts a semiconductor laser with a wavelength of 635 nm, an output power of 100 mW, a butterfly package, and an optical fiber lead-out. The laser module 1 has a power supply voltage of 0-10 V and a maximum power supply current of 0.2 A. As shown in FIGS. 5-6, the output optical fiber of the laser module 1 is connected to the optical fiber interface 2 of the laser. The optical fiber interface 2 can be an SMA 905 interface or an FC/PC interface, which can be set on the front panel of the laser. The laser module 1 is installed on a device with a Thermo Electric Cooler (TEC for short) and a heat sink. There are heat dissipating windows capable of air flow at the front and rear of the laser, and a heat dissipating fan 3 is provided in the laser.

The power supply module includes a power supply controller 4, a power supply bus 5, and an independent power supply connector 6. The power supply controller 4 has a built-in power supply chip which is used to allocate the voltage and current transmitted by the external DC power source through the power supply bus 5 to the laser module 1 according to the control signal transmitted by the upper computer, and control the power. In this example, the power supply controller 4 can reduce the 24 V voltage to 0-10 V and provide it to the laser module 1. The power supply chip can also be used for temperature control to control the temperature of the TEC and the opening and closing of the heat dissipating fan 3. The power supply controller 4 is connected to the independent power supply connector 6 through the power supply bus 5, the independent power supply connector 6 is an independent power supply interface of the laser, and is connected to an external power source.

The power supply bus 5 is provided with a power supply branch line 7, and the outer end of the power supply branch line 7 is provided with a parallel power supply connector 8. The parallel power supply connector 8 is a common power supply connector between lasers, which is used to combine multiple lasers when the output of more lasers with different wavelengths and powers is required. The parallel power supply connector 8 is used to connect multiple lasers. Only one external power source is needed for supplying power for multiple lasers, achieving the technical effect of controlling multiple laser combinations by single power source. The parallel power supply connector 8 corresponds to the power supply branch line 7 one-to-one. If the number of the power supply branch line 7 is one, each laser can only be externally connected to one laser. In this example, the number of the power supply branch line 7 is preferably 2-5. One side of the laser must be reserved for emitting lasers. Taking the number of power supply line 7 as 2, for example, one laser can be connected two lasers in parallel at the same time to form a combination of 3 lasers with different powers and wavelengths. The lasers on both sides can also be used for connecting additional lasers, and so on, to form a multi-laser combination. Since the present technology adopts bus power supply, the voltage on the bus is constant, and the laser modules are connected in parallel through the bus power supply, removing or increasing the number of laser modules will not affect the bus voltage, but only change the bus current. Therefore, stable power supply can be achieved as long as the rated output current of the power source is larger than the current needed for total laser modules.

Figure 3:
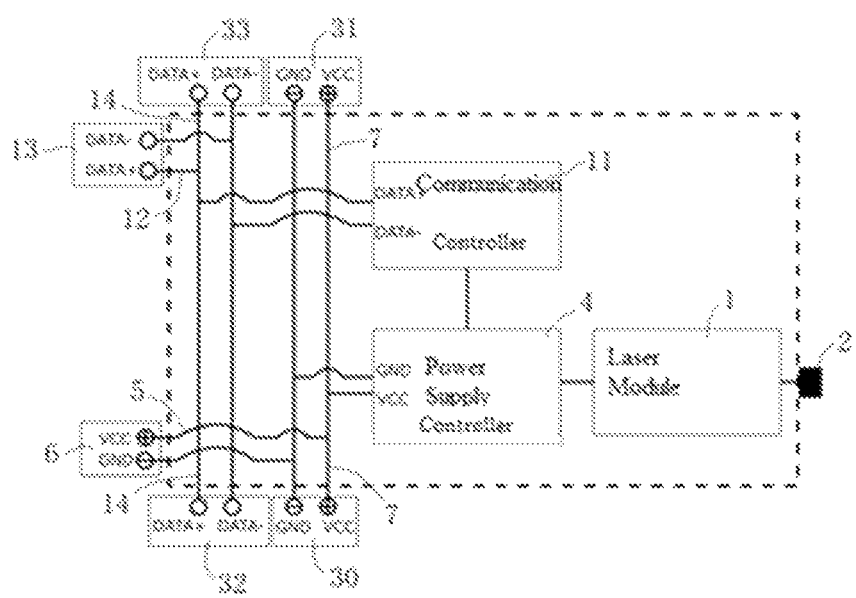
FIG. 3 is a system structure diagram of a combined multi-wavelength laser provided by another example of the present invention.

The parallel power supply connector 8 has two connection forms, one is surface attaching connection, such as plane attaching, inclined surface attaching, spherical attaching, etc.; the other is multi-plane matching, such as concave-convex slot matching, plug-in matching, etc. Among them, as shown in FIG. 3, when there is a matching relationship, two sets of conductive branch lines need to be provided on the power supply bus 5. The two sets of conductive branch lines are connected to different parallel power supply connectors 8, respectively, for example, a set of conductive branch lines is connected to the first parallel power supply connector 30, and another set of conductive branch lines is connected to the second parallel power supply connector 31. The first parallel power supply connector 30 and the second parallel power supply connector 31 have a matching relationship, so that the parallel power supply between multiple lasers can be realized.

Figure 4:
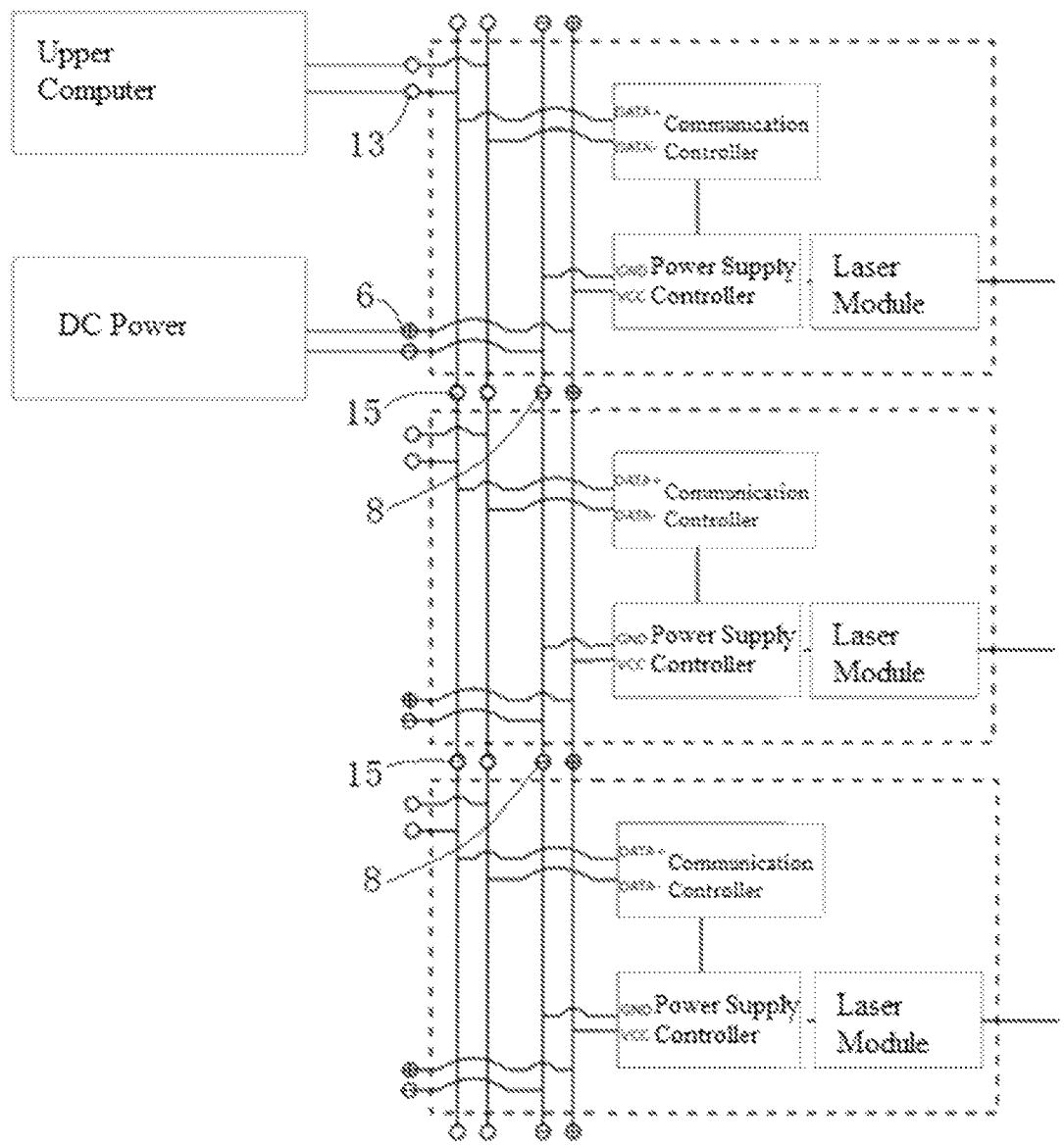
FIG. 4 is a system structure diagram of the parallel combination application of the combined multi-wavelength laser described in FIG. 3.
Figure 7:
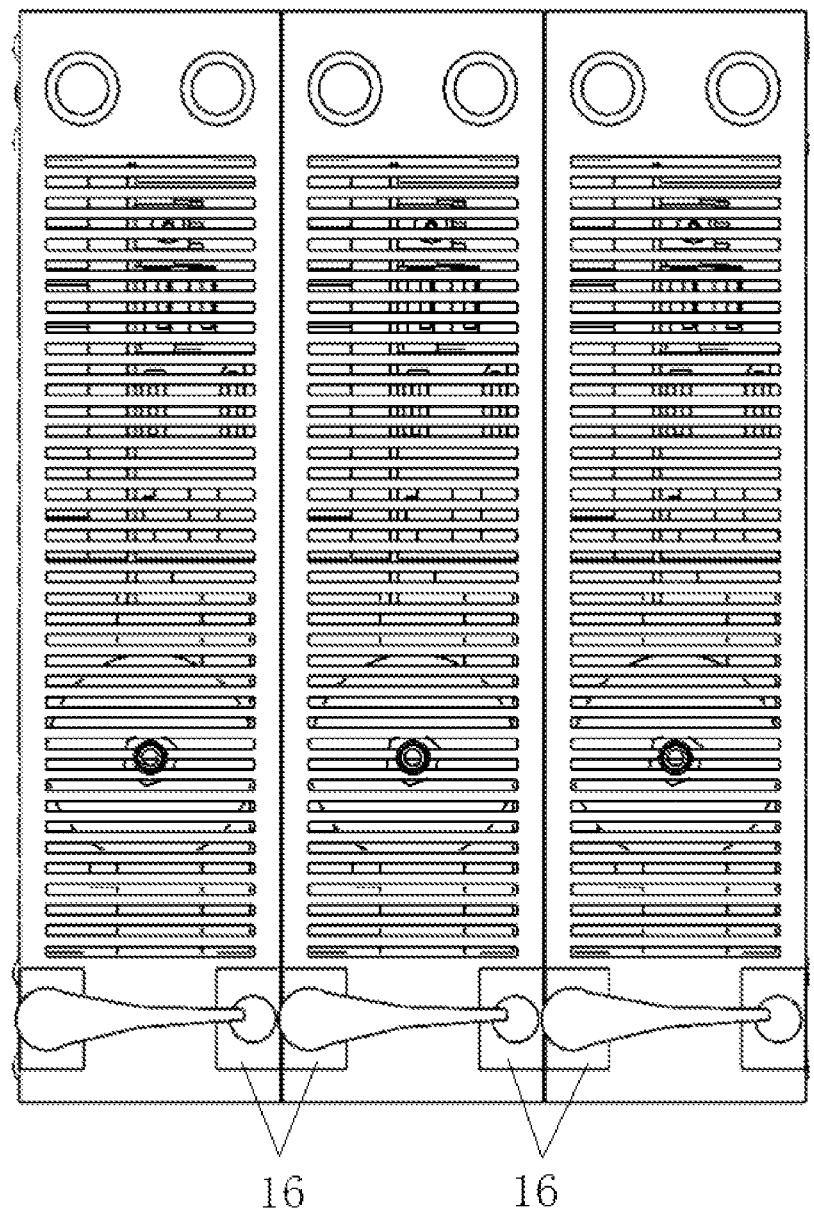
FIG. 7 is a parallel combination diagram of a product of a combined multi-wavelength laser provided by an example of the present invention.

Specifically, as shown in FIGS. 4 and 7, when the output of more lasers with different wavelengths and powers are required, multiple lasers need to be combined. The wavelengths of the lasers are 405 nm, 635 nm, and 680 nm, respectively, and the output laser powers of the three lasers are all 100 mW, and the maximum power requirement of all lasers is 3 W. An independent power supply interface for one of the lasers (e.g., with a wavelength of 405 nm) was connected to a 12 V, 1A DC power source which is capable of meeting the operational requirements of the 4 lasers. The second laser (e.g., with a wavelength of 635 nm) is interconnected with the parallel power supply connecter 8 for the first laser (with a wavelength of 405 nm), and the third module (with a wavelength of 680 nm) can be connected to the first laser or the second laser with a same way of connection as aforementioned. Finally, a parallel power supply of 3 lasers is formed, and the three lasers are powered by one power source, which can output multi-wavelength lasers at the same time. For example, the power supply voltage of the laser module 1 is 0-10 V, and the maximum power supply current is 0.2 A. The independent power supply connector 6 is connected to an external DC power source with a voltage of 12 V and a maximum power source current of 1 A. This DC power source can meet the power supply requirements of as many as four lasers in parallel.

When more laser wavelengths are needed (for example, with a wavelength of 780 nm), a newly added laser (with a wavelength of 780 nm) can be connected to any laser with idle parallel power supply connector 8 in the above-mentioned laser combination to form a parallel power supply of 4 lasers. If more modules beyond the power supply range of the power source are needed, another DC power source can be connected to the independent power supply interface (independent power supply connector 6) of any laser to realize the access of more modules. In addition, when one of the unit modules needs to be replaced (for example, when one of the modules is damaged, or when a different wavelength and power is required), the parallel power supply connector 8 of that laser can be disconnected, and the laser can be replaced or taken out.

The laser can be provided with a power supply indicator 9 and a light emitting indicator which are both connected to the power supply controller 4, and the power supply controller 4 controls the opening and closing of the power supply indicator 9 and the light emitting indicator The power supply indicator 9 is used to demonstrate whether the laser is in a power supply state, and the light emitting indicator 10 is used to demonstrate whether the laser is in a light emitting state.

As shown in FIGS. 1-2, the communication module includes a communication controller 11, a communication bus 12, and an independent communication connector 13. The communication controller 11 is connected to the independent communication connector through the communication bus 12. A communication branch line 14 is provided on the communication bus 12, and a parallel communication connector 15 is provided at the outer end of the communication branch line 14. The independent communication connector 13 is an independent communication interface of the laser, which is connected to the upper computer to provide serial control signals. The communication controller 11 receives the control signal of the upper computer through the independent communication connector 13, analyzes and processes the serial signal of the upper computer, and sends it to the power supply module. For example, the power supply controller 4 sets 0-10V voltages to the laser, achieving control over the laser's power. In this technology, due to the use of bus communication, the communication mode of the system will not change when laser modules are added or removed. Each laser has an independent number in the control chip, and the laser module is identified according to the communication number.

The parallel communication connector 15 has 2 connection forms, one is surface attaching connection, such as plane attaching, inclined surface attaching, spherical attaching, etc.; the other is multi-plane matching, such as concave-convex slot matching, plug-in matching, etc. Among them, as shown in FIG. 3, when there is a matching relationship, two sets of conductive branch lines 14 need to be provided on the communication bus 12. The two sets of conductive branch lines 14 are connected to different parallel communication connector 15, respectively, for example, a set of conductive branch lines 14 is connected to the first parallel communication connector 32, and another set of conductive branch lines 14 is connected to the second parallel communication connector 33. The first parallel communication connector 32 and the second parallel communication connector 33 have a matching relationship, so that the parallel communication between multiple lasers can be realized. As shown in FIGS. 4 and 7, as in the example of the combination of three lasers in parallel described above, the independent communication connector 13 of one of the lasers is connected to the upper computer, and the parallel communication connector 15 of the laser is connected to the laser to form a parallel communication combination of multiple lasers, so as to realize a connection between a communication bus 12 and multiple lasers and realize communication interaction.

Figure 8:
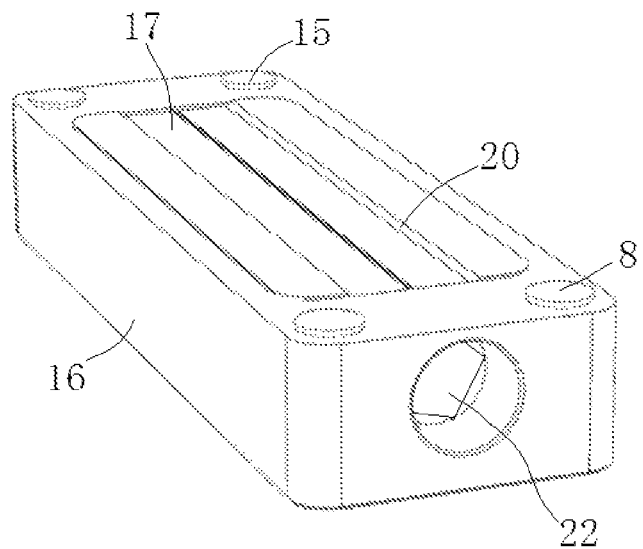
FIG. 8 is a product structure diagram of a mechanical connector of a combined multi-wavelength laser according to an example of the present invention.
Figure 9:
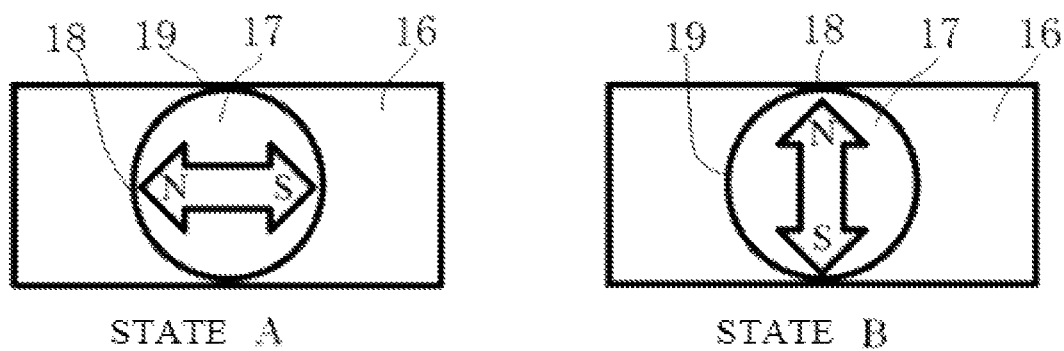
FIG. 9 is a diagram of two states of the magnet in FIG. 8. In the figure, state A is a non-attached state, and state B is an attached state.

The connection between the lasers needs to be stable, so a physical fixed connection way needs to be added between the lasers. In this example, the combined multi-wavelength laser is provided with a mechanical connector 16 that can be easily detached, such as a bayonet or magnetic attraction. The mechanical connector member 16 is used for the fixed connection between the two combined wavelength lasers. In this example, the way of magnetic attraction is preferred, and the details are as follows:

As shown in FIGS. 8-9, the mechanical connector 16 is provided with a rotatable magnet 17 and a rotating structure that controls the rotation of the magnet 17, and the magnet 17 is provided with a magnetic surface 18 and a non-magnetic surface 19. The magnetic surface 19 may be a non-magnetic surface 18 or a magnetically neutralized surface, and the connecting side of the mechanical connector 16 is provided with a slot-shaped structure 20 exposing the magnet 17. The rotating structure controls the rotation of the magnet 17. The magnet 17 has different exposed surfaces in slot-shaped structure 20 due to its rotation. It switches between the magnetic surface 18 and the non-magnetic surface 19 so as to realize the controllable magnetic attraction. Specifically, as shown in the state A in FIG. 9, the non-magnetic surface 19 of the magnet 17 is exposed in the slot-shaped structure 20. At this time, the magnetic pole is far away from the surface, and the magnetic attraction force becomes too small to be attracted; as shown in the state B in FIG. 9, after rotating the magnet 17 for 90°, the magnetic surface 18 of the magnet 17 is exposed in the slot-shaped structure 20. At this time, the magnetic pole is close to the surface, and the magnetic attraction force becomes larger, which produces attraction.

Figure 10:
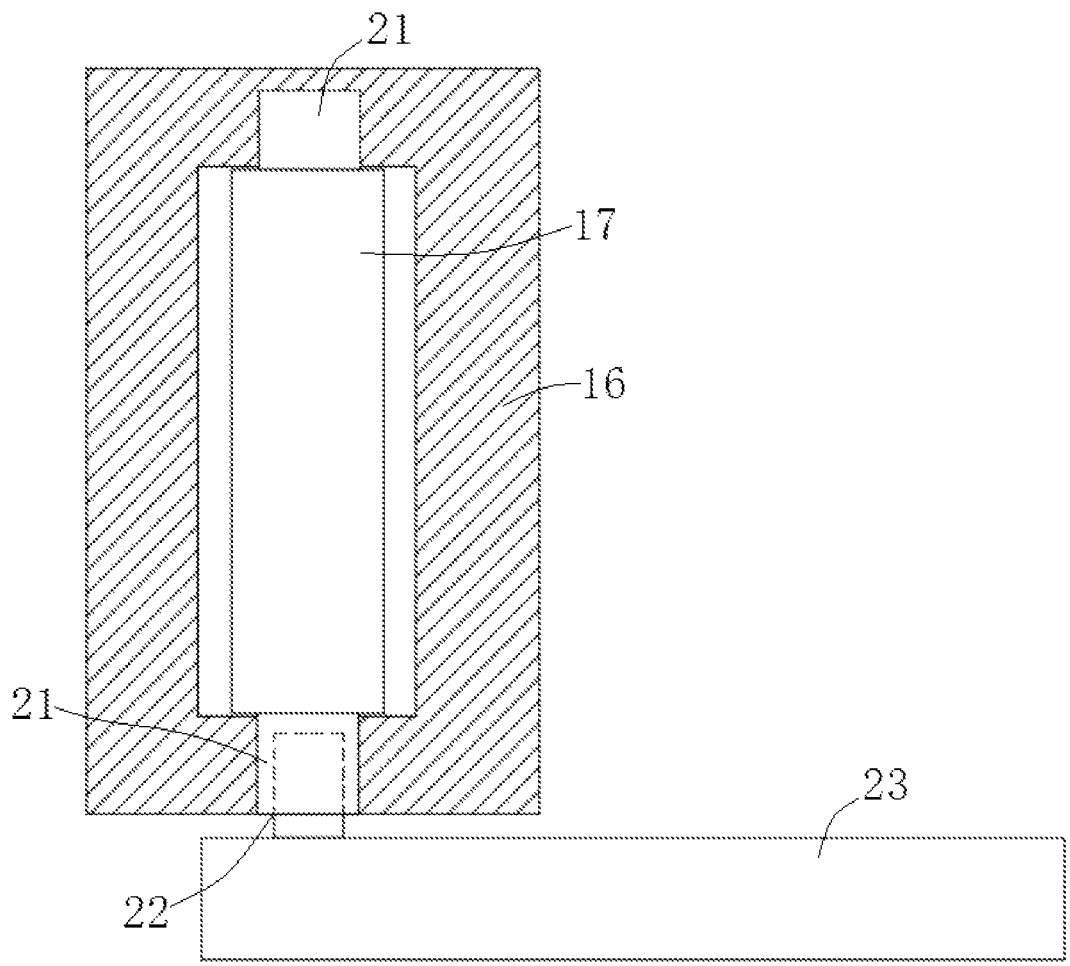
FIG. 10 is an internal structure diagram of a mechanical connector provided by an example of the present invention.

As shown in FIGS. 8 and 10, the rotating structure includes a rotating shaft 21 located on both sides of the magnet 17. The rotating shaft 21 can be an integral structure with the magnet 17. The shaft diameter of the rotating shaft 21 is preferably smaller than that of the magnet 17 which can better fix the axial movement of magnet 17. The rotating shaft 21 is rotatably connected with the mechanical connector 16. The rotating shaft 21 is provided with a non-circular groove 22, and the mechanical connector 16 is provided with a through hole exposing the non-circular groove 22. A crank 23 is inserted into the non-circular groove 22, and the crank 23 is inserted into the non-circular groove 22 for fitting with it. The rotation of the magnet 17 can be controlled by rotating the crank 23.

Figure 11:
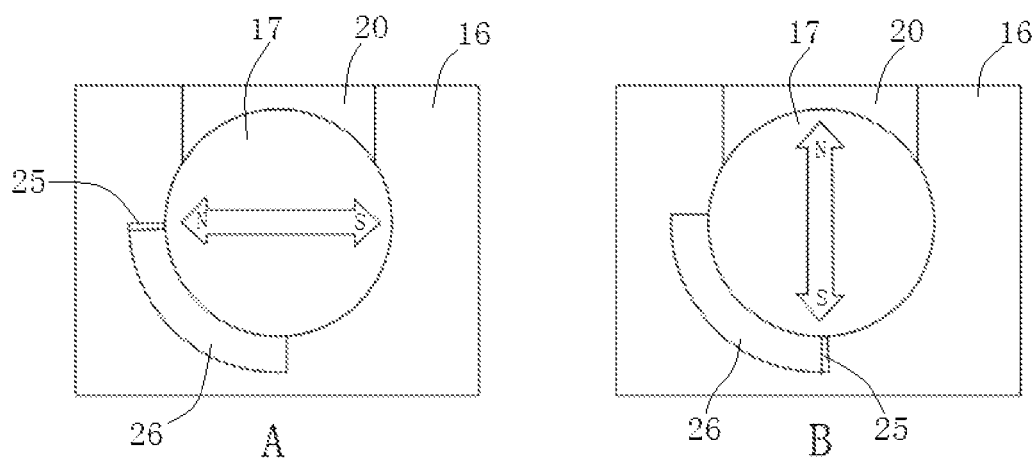
FIG. 11 is a state diagram of a magnet of a mechanical connector provided by an example of the present invention.

The rotating shaft 21 is provided with a limiting protrusion, the mechanical connector 16 is provided with an arc-shaped slot 26 that matches with the limiting protrusion, and the arc-shaped slot 26 has the same arc as that corresponding to the rotation angle of the magnet 17. The limiting protrusion may be an arc-shaped protrusion 24 or a rectangular-shaped protrusion 25. The mechanical connector 16 is provided with an arc-shaped space for movement of the limiting protrusion. The arc of the arc-shaped space corresponds to the allowable rotation range of the magnet 17. Specifically, as shown in FIG. 11, when the magnet 17 is rotated to the state A, the non-magnetic surface 19 is exposed in the slot-shaped structure 20, no attraction is generated, and the rectangular-shaped protrusion 25 is blocked and cannot continue to rotate, making the magnet 17 be accurately positioned in the non-attracted state; when the magnet 17 is rotated to the state B, the magnetic surface 18 is exposed in the slot-shaped structure 20 to cause attraction, and the rectangular-shaped protrusion 25 is blocked and cannot continue to rotate, making the magnet 17 be accurately positioned in the attracted state.

Figure 12:
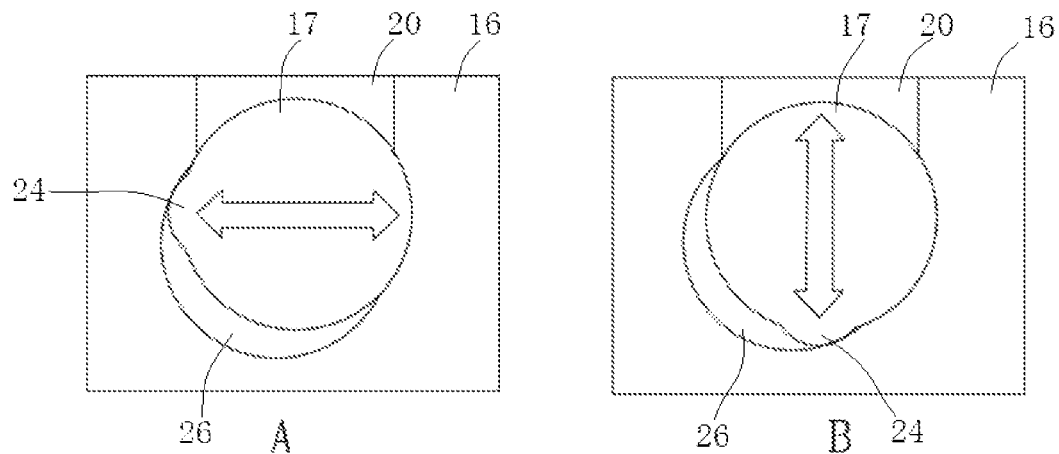
FIG. 12 is a state diagram of a magnet of a mechanical connector provided by another example of the present invention.

As shown in FIG. 12, the arc-shaped protrusion 24 is preferred in this example, which not only has an axial limitation function, but also makes the gap between the rotating axis 21 and the mechanical connector 16 to become smaller and smaller as the radius of the rotating axis 21 increases during the rotation of the magnet 17, making the connection between the two changed from gap junction to overfilled connection. Finally, the rotating shaft 21 is fixed by squeezing, so that the rotating shaft 21 must be rotated by a large external force, preventing the connection between the two lasers from being disconnected due to external forces during the connection process. When the magnet 17 is rotated to the state A, the non-magnetic surface 19 is exposed in the slot-shaped structure 20, and no attraction is generated. The arc-shaped protrusion 24 is stuck on the other side of the arc-shaped slot 26, so that so that magnet 17 can be accurately positioned in the attracted state, under which only a strong external force can make magnet 17 rotate; when the magnet 17 is rotated to the state B, the magnetic surface 18 is exposed in the slot-shaped structure 20 to cause attraction. The arc-shaped protrusion 24 is stuck on the other side of the arc-shaped slot 26 and cannot continue to rotate, so that the magnet 17 is accurately positioned in the attracted state, under which only a strong external force can make the magnet 17 rotate.

As shown in FIG. 8, in order to increase the connection between the parallel power supply connectors 8 of the two lasers, the parallel power supply connector 8 is arranged on the mechanical connector 16 so that it is located around the closest connection of the mechanical connector 16, which ensures the stability of the connection between the parallel power supply connectors 8 to the greatest extent. In this example, the parallel power supply connector 8 is a power supply contact electrode provided on the mechanical connector 16, and the side surface of the power supply contact electrode is wrapped by an insulator (such as plastic) to insulate it from the magnet 17.

As shown in FIG. 8, in order to increase the connection between the parallel communication connector 15 of the two lasers, the parallel communication connector 15 is arranged on the mechanical connector 16, so that it is located around the closest connection of the mechanical connector 16, which ensures the stability of the connection between the parallel communication connectors 15 to the greatest extent. In this example, the parallel communication connector 15 is a communication contact electrode provided on the mechanical connector 16, and the side surface of the communication contact electrode is wrapped by an insulator (such as plastic) to insulate it from the magnet 17.

Figure 13:
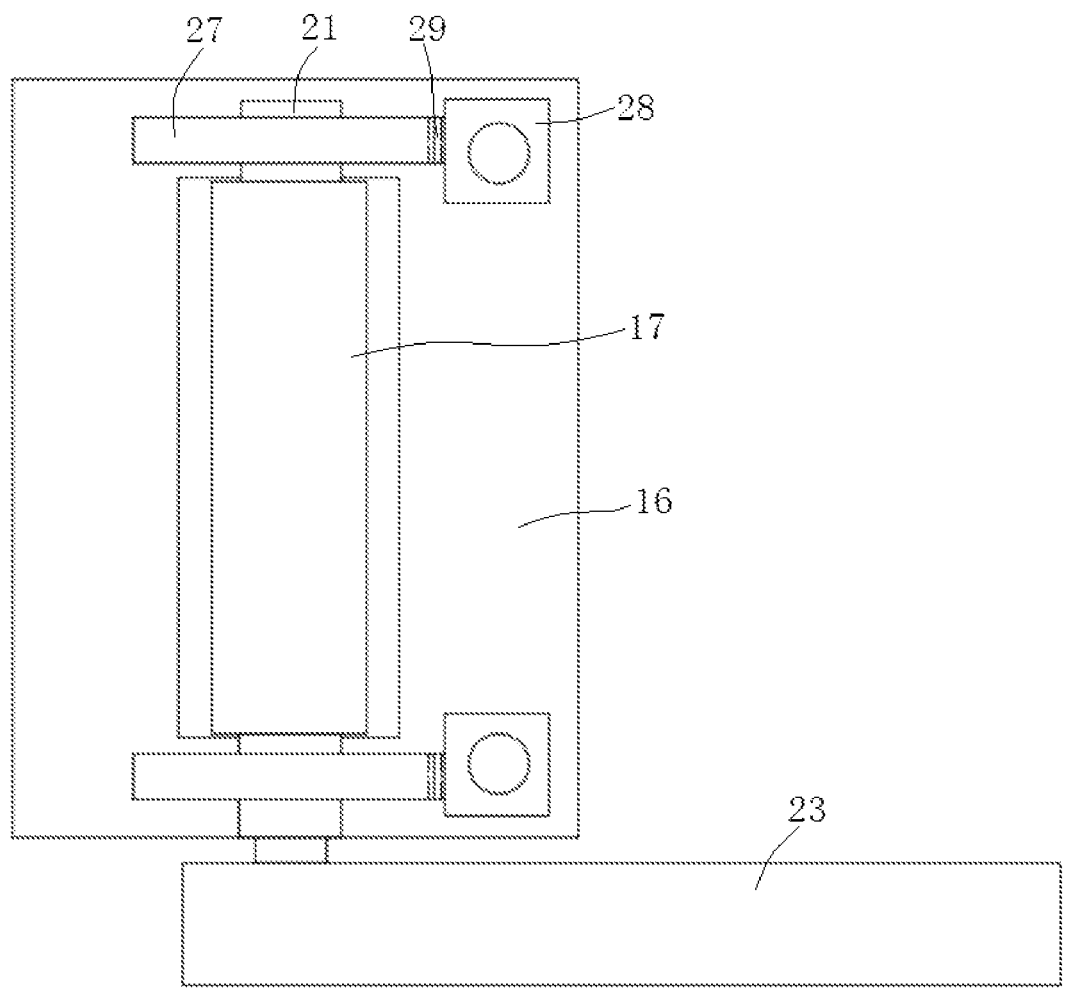
FIG. 13 is an internal structure diagram of a mechanical connector provided by another example of the present invention.

As shown in FIG. 13, in order to disconnect the connection of the parallel power supply connector 8 or the parallel communication connector 15 before the mechanical connector 16 is disconnected, a driving gear 27 is added to the rotating shaft 21. The parallel power supply connector 8 or the parallel communication connector 15 are both installed on an insulating base 28, and the insulating base 28 is provided with a driven rack 29 meshing with the driving gear 27 to realize the up and down movement of the insulating base 28. When the magnet 17 is controlled to rotate to disrupt the connection of the magnet 17, while the rotation of magnet 17, the rotating shaft 21 drives the driving gear 27 to rotate, and the driving gear 27 drives the driven rack 29 to move down, that is, the insulating base 28 moves down to achieve a large space between the two parallel power supply connectors 8 or the two parallel communication connectors 15, thereby disconnecting the two, realizing the early disconnection of the circuit or communication before the laser is mechanically disconnected, and ensuring the safety of the equipment operation.

Although the present invention has been described in detail with general descriptions and specific examples above, it is obvious to those skilled in the art that some modifications or improvements can be made on the basis of the present invention. Therefore, these modifications or improvements made without departing from the spirit of the present invention all belong to the scope of the present invention.

The invention claimed is:

1. A combined multi-wavelength laser provided with a laser module, a power supply module, and a communication module, the power supply module is used to power the laser module and the communication module, wherein the power supply module includes a power supply controller, a power supply bus, and an independent power source connector, the power supply controller is connected to the independent power source connector via the power supply bus, the power supply bus is provided with a conductive branch line, and an outer end of the conductive branch line is provided with a wire connector;

wherein the communication module includes a communication controller, a communication bus, and an independent communication connector, the communication controller is connected to the independent communication connector through the communication bus, the communication bus is provided with a communication branch line, an outer end of the communication branch line is provided with a communication connector.

2. The combined multi-wavelength laser according to claim 1, wherein the power supply bus is provided with two sets of conductive branch lines, wherein one set of the conductive branch lines is connected to a first wire connector, and the other set of the conductive branch lines is connected to a second wire connector, and the first wire connector and the second wire connector are in a matching connection relationship with each other.

3. The combined multi-wavelength laser according to claim 1, wherein the communication bus is provided with two sets of communication branch lines, one set of the communication branch lines is connected to a first communication connector, and the other set of the communication branch lines is connected to a second communication connector, and the first communication connector and the second communication connector are in a matching connection relationship with each other.

4. The combined multi-wavelength laser according to claim 1, wherein the external of the combined multi-wavelength laser is provided with a mechanical connector, and the mechanical connector is used for a fixed connection between two combined wavelength lasers.

5. The combined multi-wavelength laser according to claim 4, wherein a rotatable magnet and a rotating structure for controlling the rotation of the magnet are provided in the mechanical connector, and the magnet is provided with a magnetic surface and a non-magnetic surface, the connecting side of the mechanical connector is provided with a slot-shaped structure exposing the magnet.

6. The combined multi-wavelength laser according to claim 5, wherein the rotating structure comprises a rotating shaft located on both sides of the magnet, and the rotating shaft is connected to the mechanical connector in rotation, and the rotating shaft is provided with a non-circular groove, a through hole exposing the non-circular groove is provided on the mechanical connector, and a crank is inserted into the non-circular groove.

7. The combined multi-wavelength laser according to claim 6, wherein the rotating shaft is provided with a limiting protrusion, and the mechanical connector is provided with an arc-shaped slot that matches with the limiting protrusion, the arc of the arc-shaped slot is the same as the arc corresponding to the rotation angle of the magnet.

8. The combined multi-wavelength laser according to claim 6, wherein the power source connector or communication connector is provided on the mechanical connector.

9. The combined multi-wavelength laser according to claim 8, wherein the rotating shaft is provided with a driving gear which meshes with a driven rack, and the driven rack is fixed on one side of an insulating base, the parallel power supply connector or parallel communication connector is installed on the insulating base.

* * * * *